United States Patent
Kakiuchi et al.

(10) Patent No.: US 9,636,463 B2
(45) Date of Patent: May 2, 2017

(54) COMBINATION CONTAINER/SYRINGE

(75) Inventors: Makoto Kakiuchi, Takahagi (JP); Harumi Kakiuchi, legal representative, Takahagi (JP); Seiji Shimazaki, Takahagi (JP)

(73) Assignee: ARTE CORPORATION, Tokyo (JP)

( * ) Notice: Subject to any disclaimer, the term of this patent is extended or adjusted under 35 U.S.C. 154(b) by 800 days.

(21) Appl. No.: 13/983,298

(22) PCT Filed: Feb. 2, 2012

(86) PCT No.: PCT/JP2012/052359
§ 371 (c)(1),
(2), (4) Date: Aug. 1, 2013

(87) PCT Pub. No.: WO2012/105640
PCT Pub. Date: Aug. 9, 2012

(65) Prior Publication Data
US 2014/0048432 A1    Feb. 20, 2014

(30) Foreign Application Priority Data
Feb. 2, 2011   (JP) .................................. 2011-021006

(51) Int. Cl.
*A61M 5/28*   (2006.01)
*A61J 1/00*   (2006.01)
(Continued)

(52) U.S. Cl.
CPC ................ *A61M 5/286* (2013.01); *A61J 1/00* (2013.01); *A61M 5/347* (2013.01);
(Continued)

(58) Field of Classification Search
CPC ............ A61M 5/286; A61M 2005/287; A61M 2005/3132; A61M 2005/3123
See application file for complete search history.

(56) References Cited

U.S. PATENT DOCUMENTS 2,591,046 A    4/1952 Brown
4,439,184 A *  3/1984 Wheeler ............... A61M 3/005
                                                       604/191

(Continued)

FOREIGN PATENT DOCUMENTS

CN    1080874      1/1994
CN    1080874 A    1/1994

(Continued)

OTHER PUBLICATIONS

European Search Report issued in EP Application No. 12741652.7-1662 dated Mar. 4, 2015, 6 pages.

(Continued)

*Primary Examiner* — Andrew Gilbert
(74) *Attorney, Agent, or Firm* — Nixon Peabody, LLP; Khaled Shami

(57) ABSTRACT

A combination container/syringe (1) provided with an outer cylinder (10) that forms a cylindrical shape centered on an axial line (O); a front stopper that is inserted into a distal end side of the outer cylinder (10); and a cylindrical tip (50) that is fitted to an outer periphery of the distal end of the outer cylinder via a fitting hole (61) at a base end side, and that has a bypass chamber (71) that houses the front stopper at a front side of the fitting hole, in which an inner diameter of the bypass chamber is formed larger than an outer diameter of the front stopper, and a plurality of ribs (74) that protrude toward an inside in a radial direction and extend in the direction of the axial line to make close contact with the outer peripheral surface of the front stopper that has moved to the inside of the bypass chamber are provided spaced apart in a circumferential direction on the inner peripheral surface (73) of the bypass chamber. According to this combination container/syringe, it is possible to effectively eliminate air bubbles in a medicinal solution via a medicinal solution flow-through space that is formed over the circum- (Continued)

ferential direction between the inner peripheral surface of the bypass chamber and the outer peripheral surface of the front stopper.

3 Claims, 6 Drawing Sheets

(51) Int. Cl.
  *A61M 5/34* (2006.01)
  *A61M 5/31* (2006.01)
(52) U.S. Cl.
  CPC ............... *A61M 2005/287* (2013.01); *A61M 2005/3104* (2013.01); *A61M 2005/3123* (2013.01); *A61M 2005/3132* (2013.01)

(56) References Cited

U.S. PATENT DOCUMENTS

| | | | | |
|---|---|---|---|---|
| 4,496,344 A * | 1/1985 | Kamstra | ............... | A61M 5/284 604/191 |
| 5,665,068 A * | 9/1997 | Takamura | ............... | A61M 5/284 206/221 |
| 5,741,236 A * | 4/1998 | Kakiuti | ................. | A61M 5/001 604/192 |
| 6,966,897 B2 * | 11/2005 | Shimazaki | .......... | A61M 5/3129 604/110 |
| 7,699,811 B2 * | 4/2010 | Hasegawa | ........... | A61M 5/3134 604/122 |
| 2002/0052577 A1 * | 5/2002 | Shimazaki | .......... | A61M 5/3129 604/192 |
| 2003/0034264 A1 * | 2/2003 | Hamai | ..................... | A61L 2/04 206/364 |
| 2007/0161961 A1 * | 7/2007 | Hasegawa | ........... | A61M 5/3134 604/187 |
| 2008/0091148 A1 * | 4/2008 | Shimazaki | ............ | A61M 5/284 604/218 |
| 2008/0188816 A1 * | 8/2008 | Shimazaki | .............. | A61M 5/34 604/240 |
| 2010/0137800 A1 * | 6/2010 | Kakiuchi | .............. | A61M 5/286 604/125 |

FOREIGN PATENT DOCUMENTS

| | | |
|---|---|---|
| CN | 93103976 | 1/1994 |
| CN | 2860495 Y | 1/2007 |
| EP | 2213322 | 8/2010 |
| JP | 04-012990 Y2 | 3/1992 |
| JP | 07-039582 A | 2/1995 |
| JP | 2005-131216 A | 5/2005 |
| JP | 2007-111156 A | 5/2007 |
| WO | 2007/099870 A1 | 9/2007 |
| WO | WO2010/139793 A1 | 12/2010 |

OTHER PUBLICATIONS

Search Report in Office Action in Chinese application No. 201280007035.7 dated Aug. 26, 2014.
International Search Report in Application No. PCT/JP2012/052359, mailed on May 1, 2012.

* cited by examiner

COMBINATION CONTAINER/SYRINGE

CROSS REFERENCE TO RELATED APPLICATIONS OR PRIORITY CLAIM

This application is a National Phase of PCT/JP2012/052359, filed Feb. 2, 2012, entitled, "Combination Container/Syringe" which claims the benefit of Japanese Patent Application No. 2011-021006, filed Feb. 2, 2011, the contents of which are incorporated herein by reference in their entirety.

TECHNICAL FIELD

The present invention relates to a combination container/syringe in which a medicinal solution is pre-filled, and that at the time of use can be immediately used by being removed from its packaging.

BACKGROUND ART

A combination container/syringe can be used immediately after being unpackaged without performing troublesome procedures at medical institutions due to the fact that a medicinal solution has been prefilled. In this way, since the combination container/syringe is very convenient, it substantially lightens the workload of people involved in medical service such as physicians and nurses. For this reason, it has been adopted by many medical institutions.

Conventionally, as this combination container/syringe, there is known one that is provided with an outer cylinder, a front stopper and end stopper that are inserted into the outer cylinder from the front and rear end sides and that liquid-tightly seal the medicinal solution that is filled in the outer cylinder, a cylindrical tip that is fitted on the distal end of the outer cylinder from the outer side and in which are provided a bypass chamber that the front stopper enters and a luer tip for attaching the injection needle at the distal end thereof, a finger grip that is fitted from the outer side on the rear end of the outer cylinder, and a plunger rod that is inserted in the outer cylinder from the rear end portion of the outer cylinder and that is coupled to the end stopper (for example, refer to Patent Document 1).

When using this kind of combination container/syringe, by pushing the end stopper into the outer cylinder with the plunger rod, the front stopper moves forward together with the medicinal solution. When the front stopper is pushed out from the outer cylinder and enters into the bypass chamber at the cylindrical tip, the distal end-side seal of the medicinal solution that is sealed between the front stopper and the end stopper is released. Thereby, the medicinal solution flows out from the inside of the outer cylinder into the bypass chamber, and by being guided to the inner surface of the luer tip along the bypass groove that is provided at the inner peripheral surface of the bypass chamber, is guided to the injection needle.

PRIOR ART DOCUMENTS

Patent Documents

[Patent Document 1] Japanese Unexamined Patent Application, First Publication No. 2007-111156

DISCLOSURE OF THE INVENTION

Problems to be Solved by the Invention

Generally, in an injection, which is a medical act that involves directly injecting a medicinal solution into a necessary location in the body by a syringe, in order to prevent air bubbles mixed in the medicinal solution from being injected into the body of the patient, an air bubble removal operation is performed by slightly pushing the plunger rod into the outer cylinder as a stage prior to injection. By this operation, in the aforementioned combination container/syringe, air bubbles in the outer cylinder pass through the bypass groove to be discharged from the distal end of the injection needle to outside of the syringe.

Here, in the aforementioned conventional combination container/syringe, in order to reduce the residual amount of a medicinal solution in the bypass groove, the width of the bypass groove through which the medicinal solution and air bubbles pass is made as small as possible.

However, when attempting to discharge air bubbles to the outside by pushing the plunger rod into the outer cylinder after concentrating the air bubbles remaining behind in the outer cylinder at the upper surface of the medicinal solution by pointing the distal end side of the combination container/syringe upward, the medicinal solution that is further below the air bubbles enters the bypass groove ahead of some of the air bubbles that remain above due to the influence of surface tension of the medicinal solution. Thereby, since the medicinal solution blocks the passageway of the air bubbles, some of the air bubbles disperse in the bypass groove and remain behind, and so there is the risk of them being mixed with the medicinal solution that is to be subsequently injected and thereby being injected into the body of a patient. Accordingly, in order to reliably remove the air bubbles that have dispersed and remain in the bypass groove, it is necessary to further push the plunger rod into the outer cylinder, and as a result, the amount of wasted medicinal solution that is discharged to the outside of the syringe together with the air bubbles increases.

This present invention was achieved in view of the above circumstances, and has as its object to provide a combination container/syringe that can effectively remove air bubbles in a medicinal solution.

Means for Solving the Problems

In order to solve the aforementioned issues, this invention provided the following means.

That is, the combination container/syringe according to the present invention is provided with: an outer cylinder that forms a cylindrical shape extending along an axial line; a front stopper that is inserted into a distal end side of the outer cylinder; an end stopper that is inserted into a rear end side of the outer cylinder, and that seals a medicinal solution in a space with the front stopper; a cylindrical tip that is fitted to an outer periphery of the distal end of the outer cylinder via a fitting hole at a base end side, and that is provided with a bypass chamber that houses the front stopper at the distal end side of the fitting hole, and provided with a luer tip for attaching an injection needle; a finger grip that is fitted on the rear end side of the outer cylinder; and a plunger rod that is inserted in the outer cylinder from the rear end side of the outer cylinder to be coupled to the end stopper, in which an inner diameter of the bypass chamber is formed larger than an outer diameter of the front stopper, and on an inner peripheral surface having a circular cross section of the bypass chamber, a plurality of ribs that protrude toward an inside in a radial direction and extend over the entire region in the axial line direction of the bypass chamber to be capable of making close contact with an outer peripheral surface of the front stopper that has moved to the inside of the bypass chamber are provided spaced apart in a circumferential direction.

When performing air bubble elimination in the combination container/syringe having these characteristics, the combination container/syringe is held in a state of the distal end side of the combination container/syringe being pointed upward. Thereby, the air bubbles in the medicinal solution are concentrated at the upper surface of the medicinal solution.

When the front stopper is made to advance along with the end stopper by pushing the plunger rod into the outer cylinder in this state, the front stopper that has been fitted in the outer cylinder moves into the bypass chamber.

At this time, when the front stopper is supported in the bypass chamber by the ribs formed in the bypass chamber by making close contact with the front stopper, a medicinal solution flow-through space whose dimension in the radial direction is uniform along the circumferential direction is formed between the outer peripheral surface of the front stopper and the inner peripheral surface of the bypass chamber.

Thereby, the air bubbles that have concentrated at the rear end surface of the front stopper are introduced to the medicinal solution flow-through space, and thereby guided to the luer tip to be expelled to the outside without being influenced by the surface tension of the medicinal solution.

Note that in the case of for example a groove for circulating the medicinal solution being formed in the inner peripheral surface of the bypass chamber, while there is a possibility of air bubbles remaining behind in this groove, in the present invention, since the inner peripheral surface of the bypass chamber has a circular cross section and is formed smoothly over the circumferential direction, there is no remaining behind of air bubbles on this circumferential surface.

Also, since the ribs are formed over the entire region in the axial line direction of the inner peripheral surface of the bypass chamber, when the front stopper has moved completely into the bypass chamber, the medicinal solution flow-through space is formed over the entire region in the axial line direction of the bypass chamber. Thereby, it is possible to lead the medicinal solution and air bubbles to the luer tip more smoothly.

Effects of the Invention

According to the combination container/syringe of the present invention, since the medicinal solution flow-through space is formed over the circumferential direction between the inner peripheral surface of the bypass chamber and the outer peripheral surface of the front stopper, it is possible to expel air bubbles to the outside via the medicinal solution flow-through space without being influenced by the surface tension of the medicinal solution. Thereby, it becomes possible to effectively eliminate air bubbles in the medicinal solution.

BEST MODE FOR CARRYING OUT THE INVENTION

Hereinbelow, a combination container/syringe 1 according to an embodiment of the present invention shall be described with reference to the drawings.

Figure 1:
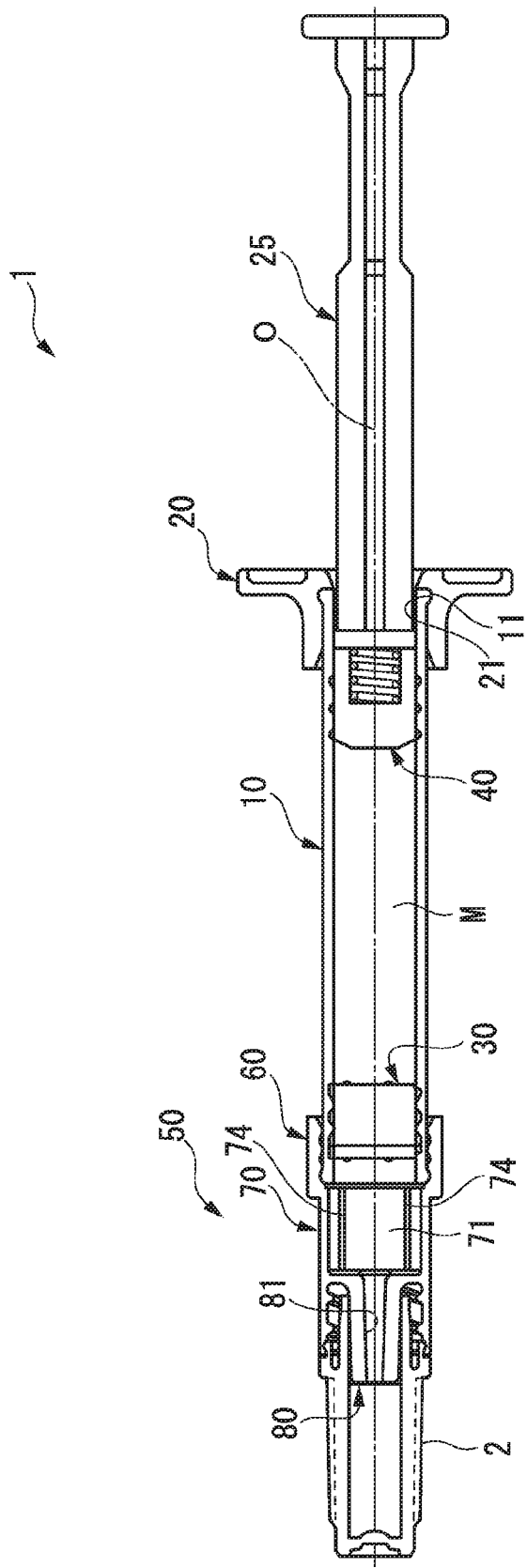
FIG. 1 is a longitudinal cross-sectional drawing of a combination container/syringe according to an embodiment of the present invention.

As shown in FIG. 1, the combination container/syringe 1 is provided with an outer cylinder 10, a cylindrical tip 50 that is attached to a distal end side thereof (the left side in FIG. 1), a finger grip 20 that is fitted from an outer side on the outer periphery of a rear end side of the outer cylinder 10 (the right side in FIG. 1), a front stopper 30 that seals a medicinal solution M that has been filled in the outer cylinder 10 from a distal end side, an end stopper 40 that seals the medicinal solution M from the rear end side, and a plunger rod 25 that is inserted in the outer cylinder 10 from the rear end side so that the distal end portion thereof is coupled to the end stopper 40, and that causes the end stopper 40 to move back and forth in an axial line O direction of the outer cylinder.

The outer cylinder 10 is made of transparent glass and forms a cylindrical shape extending along the axial line O, with the medicinal solution M filled in the interior, and the distal end side thereof being sealed by the front stopper 30, and the rear end side being sealed by the end stopper 40.

A ring-shaped protrusion 11 is provided on the rear-end outer circumference of the outer cylinder 10, and the finger grip 20 is firmly fixed to the outer cylinder 10 by engaging the ring-shaped protrusion 11 with a ring-shaped groove 21 that is formed in the circular hole portion of the finger grip 20.

Note that the finger grip 20, in addition to a constitution that is separately attached to the outer cylinder 10, may also be integrally formed with the outer cylinder 10.

Figure 2:
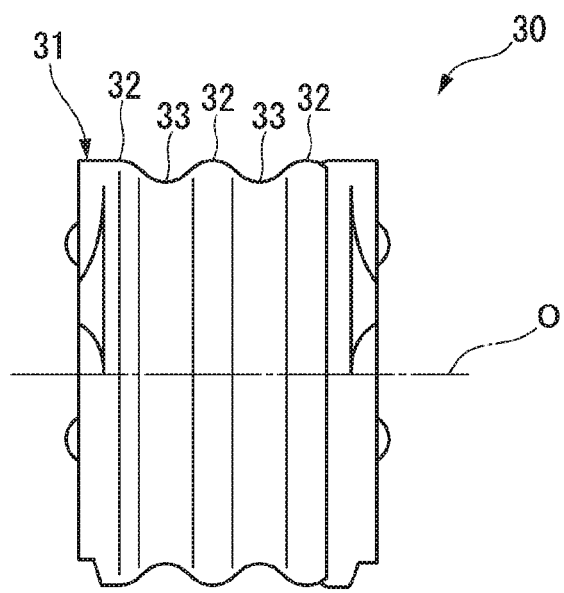
FIG. 2 is an enlargement of the front stopper in FIG. 1.

As shown in greater detail in FIG. 2, the front stopper 30 is formed from a medical rubber that has corrosion resistance to the medicinal solution M and has a substantially cylindrical shape centered on the axial line O.

On an outer peripheral surface 31 of this front stopper 30, an annular convex portion 32 that protrudes to the outer side in the radial direction and an annular concave portion 33 that concaves in an annular shape toward the inside in the radial direction are alternately formed in a continuous manner in the axial line O direction along the entire circumference of the outer peripheral surface 31. The front stopper 30 of the present embodiment has three of the annular convex portions 32 that are separated in the axial O direction, and has a total of two of the annular concave portions 33 that are respectively formed between these annular convex portions 32. Hereinbelow an outer diameter of the annular convex portion 32 designates an outer diameter of the front stopper 30.

The front stopper 30, prior to use of the combination container/syringe 1, is fitted in a liquid-tight manner in the outer cylinder 10 so as to be positioned at the distal end side within the outer cylinder 10. That is, this front stopper 30 is formed with the outer diameter thereof larger than an inner diameter of the outer cylinder 10, and so when fitted inside of the outer cylinder 10, it is put in a state of being reduced in diameter from its original outer diameter as a result of being compressed from the inner peripheral surface 73 of the outer cylinder 10.

The end stopper 40 is formed from a medical rubber that has corrosion resistance to the medicinal solution M and has a substantially cylindrical shape centered on the axial line O. This end stopper 40, prior to use of the combination container/syringe 1, is fitted in a liquid-tight manner in the outer cylinder 10 so as to be positioned at the rear end side within the outer cylinder 10.

The medicinal solution M that is to be given to the patient is sealed in the outer cylinder 10 in the space between this end stopper 40 and the front stopper 30.

As shown in FIG. 1, the plunger rod 25 is inserted in the outer cylinder 10 from the rear end side of the outer cylinder 10, and the distal end thereof is coupled to the end stopper 40.

Figure 3:
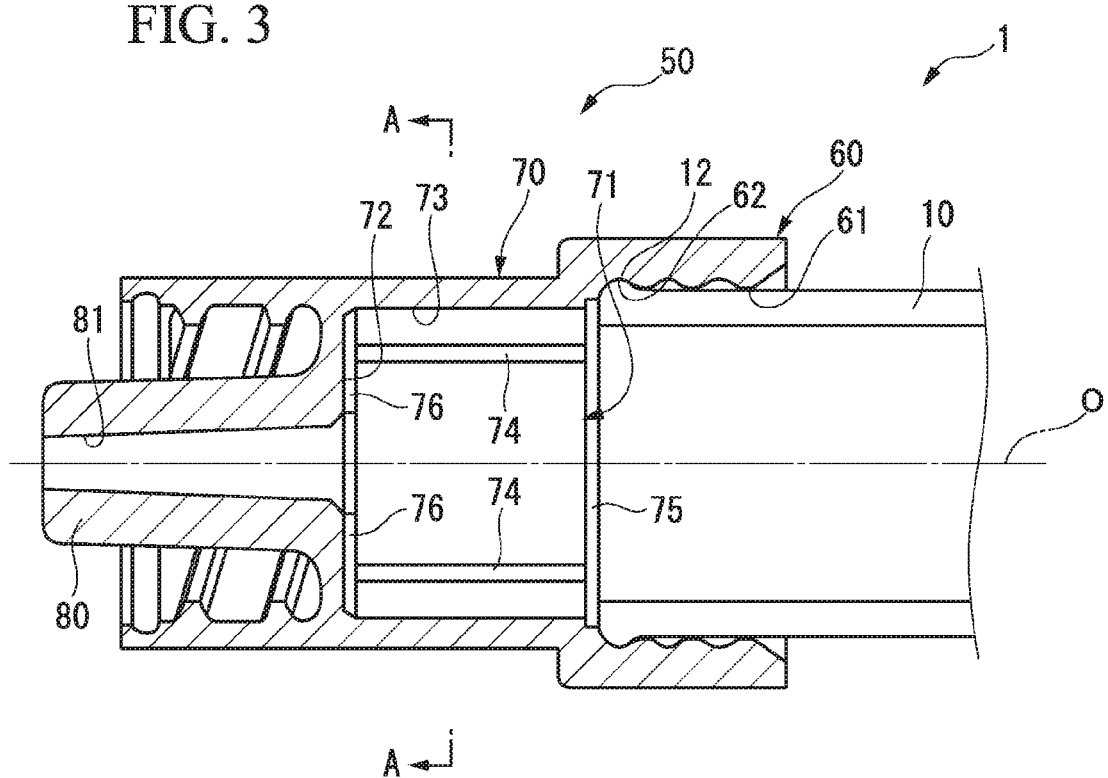
FIG. 3 is an enlargement of the cylindrical tip in FIG. 1.

The cylindrical tip 50, as shown in greater detail in FIG. 3, has a multi-stage cylindrical shape in outward form consisting of a transparent synthetic resin that is provided with moderate rigidity, and is provided with a base end portion 60 that has a cylindrical shape, a cylinder portion 70 that is coupled to the distal end side of the base end portion 60 so as to be reduced in diameter by one step, and a luer tip 80 that is formed with a smaller diameter than the cylinder portion 70 further to the distal end side of the cylinder portion 70.

At an inner side of the aforementioned base end portion 60, a fitting hole 61 that opens to the rear end side of the cylindrical tip 50 is formed, and a bottomed round hole-shaped bypass chamber 71 is formed at the distal end side of the fitting hole 61, that is to say, at the inner side of the cylinder potion 70. Note that the surface facing the rear end side in this bypass chamber 71 is made to be a bottom portion 72 that the front stopper 30 described below abuts.

Also, a guide hole 81 that penetrates the luer tip 80 along the center axis O is formed in the interior of the aforementioned luer tip 80. That is to say, one end of the guide hole 81 opens to the center of the bottom portion 72 of the bypass chamber 71, and the other end opens to the distal end of the luer tip 80. An injection needle (not illustrated) that extends to the distal end side along the axial center O is attached in a continuous state to this guide hole 81.

Note that prior to use of the combination container/syringe 1, a cover 2 that covers the cylindrical tip 50 (luer tip 80) is attached to the distal end of the cylindrical tip 50.

The fitting hole 61 is a hole that is formed for attaching the cylindrical tip 50 to the outer cylinder 10, and an inner diameter thereof is formed to be approximately the same outer diameter as the outer diameter of the outer cylinder 10. By fitting this fitting hole 61 on the distal end of the outer cylinder 10 from the outer side, the cylindrical tip 50 is attached to the distal end side of the outer cylinder 10.

Also, as shown in detail in FIG. 3, a ring-shaped groove 62 centered on the axial line O is formed at the front end portion of the inner circumferential wall of the fitting hole 61. Also, a ring-shaped projection 12 is formed on the outer circumference of the outer cylinder 10 at the distal end thereof, and when attaching the cylindrical tip 50 to the distal end side of the outer cylinder 10, the cylindrical tip 50 is firmly fixed to the outer cylinder 10 by the ring-shaped projection 12 being engaged with the ring-shaped groove 62.

The bypass chamber 71 is made to be a hole with a bottom in which an inner diameter of the inner peripheral surface 73 thereof is a smaller diameter by one step than the fitting hole 61. Particularly in this embodiment, the inner diameter of the inner peripheral surface 73 of the bypass chamber 71 is formed to be greater than an outer diameter of the outer peripheral surface 31 of the front stopper 30, that is, the original outer diameter of the front stopper 30 in the state of not being fitted in the outer cylinder 10.

Figure 4A:
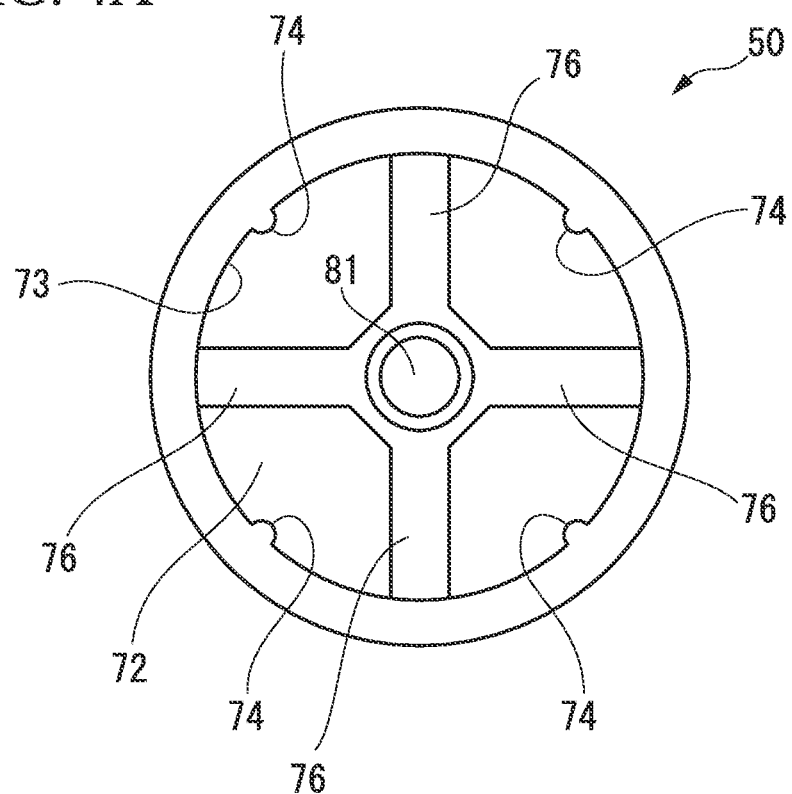
FIG. 4A is a cross-sectional view along A-A in FIG. 3.

Also, as shown in FIG. 3 and FIG. 4A, on the inner peripheral surface 73 of the bypass chamber 71, a plurality of linear ribs (ribs) 74 that protrude toward the inside in the radial direction and extend in a linear manner over the entire region in the axial line O direction of the bypass chamber 71, are formed. These linear ribs 74 extend parallel with the axial direction O and are arranged in a plurality spaced apart in the circumferential direction. In the present embodiment, four linear ribs 74 are formed at an interval of 90° in the circumferential direction. Note that it is preferred that at least three or more of the linear ribs 74 be formed, and it is more preferred that they be eight or less. Also, it is preferred that this plurality of linear ribs 74 be arranged equally spaced in the circumferential direction.

Figure 4B:
FIG. 4B is a drawing that shows a modification of the linear rib in the combination container/syringe according to the embodiment of the present invention.
Figure 4C:
FIG. 4C is a drawing that shows a modification of the linear rib in the combination container/syringe according to the embodiment of the present invention.

The height of the linear rib 74 from the inner peripheral surface 73 of the bypass chamber 71, that is, the dimension in the radial direction of the linear ribs 74, is preferably set to 0.05 to 0.45 mm. Also, the width in the circumferential direction of the linear rib 74 is preferably set to 0.3 to 0.1 mm. Note that in the case of the present embodiment, as shown in FIG. 4A, at least a distal end of the linear rib 74 in a cross section perpendicular to the axial line O is arc-shaped. However, for example, as shown in FIG. 4B or FIG. 4C, at least the distal end of the linear rib 74 in a cross section perpendicular to the axial line O may also have a triangular shape that protrudes from the inner peripheral surface 73 of the bypass chamber 71 toward the inside in the radial direction, or a trapezoidal shape whose width narrows toward the inside in the radial direction.

Also, an annular groove 75 with a circular ring shape that extends in the circumferential direction center on the axial line O is formed in the inner peripheral surface 73 of the bypass chamber 71 in the vicinity of the boundary between the bypass chamber 71 and the fitting hole 61. The rear ends of the aforementioned plurality of linear ribs 74 are respectively connected to this annular groove 75.

Moreover, a plurality of radial grooves 76 that extend in a radial shape from an opening of a guide hole 81 that is formed in the center of the bottom portion 72 toward the outer side in the radial direction are formed in the bottom portion 72 of the bypass chamber 71. The end portion at the outer side in the radial direction of this radial groove 76 is connected to the inner peripheral surface 73 of the bypass chamber 71. Also, the radial grooves 76 are arranged in a plurality at equally spaced intervals in the circumferential direction, and in the present embodiment, four radial grooves 76 are formed at an interval of 90° in the circumferential direction.

Also, as shown in FIG. 4A, the linear ribs 74 and the radial grooves 76 of the present embodiment have a positional relationship that is offset by 45° in the circumferential direction when viewed from the axial line O direction.

Here, in the case of the inner diameter of the outer cylinder 10 being D mm, the outer diameter of the front stopper 30 (the outer diameter of the annular convex portion 32) is preferably set to for example D×[1+(4.5~7.5%)] mm. Also, the inner diameter of the inner peripheral surface 73 of the bypass chamber 71 is preferably set to D+(0.8~1.7) mm.

When performing an injection on a patient using the combination container/syringe 1 having the aforementioned constitution, air bubble elimination work is performed to eliminate air bubbles that remain in the medicinal solution M. At the time of this air bubble elimination, first the combination container/syringe 1 is held in a state of the injection needle attached to the luer tip 80, and the distal end side pointed upward. Thereby, the air bubbles in the medicinal solution M become concentrated at the upper portion of the medicinal solution M, that is, in the vicinity of the rear end surface of the front stopper 30.

Then, when the plunger rod 25 is pushed into the outer cylinder 10 in this state, the pressing force is transmitted to the front stopper 30 via the medicinal solution M, and the front stopper 30 moves forward. Thereby, the front stopper 30 moves from the distal end of the outer cylinder 10 into the bypass chamber 71.

Figure 5:
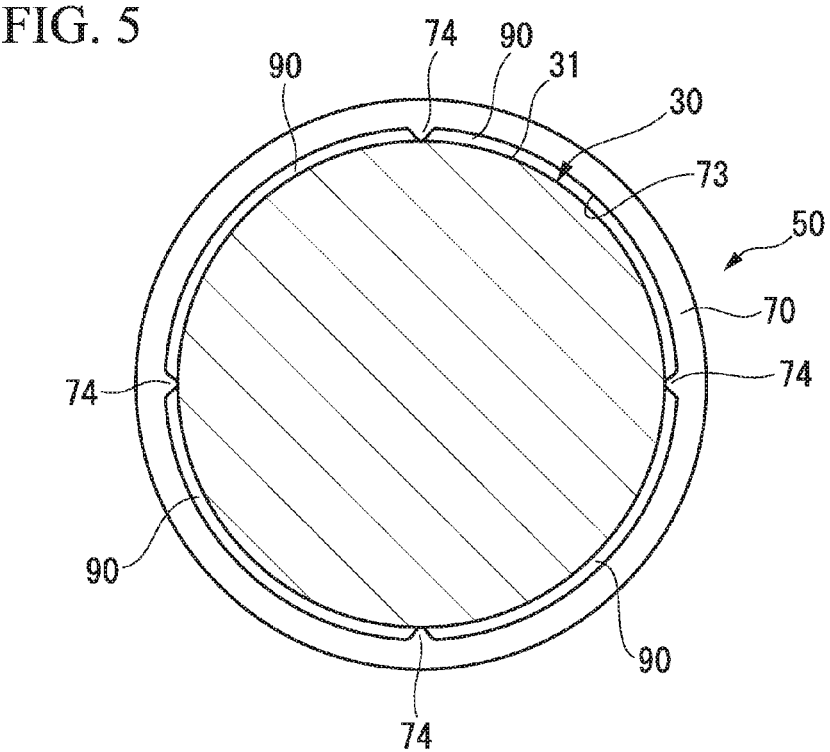
FIG. 5 is a cross-sectional view perpendicular to the axial line in the bypass chamber, and is a drawing that describes the state of the front stopper having moved into the bypass chamber.

In the state of the front stopper 30 having moved into the bypass chamber 71 in this way, as shown in FIG. 5, the distal end of the plurality of linear ribs 74 make close contact with the outer peripheral surface 31 of the front stopper 30, that is, the annular convex portion 32. At this time, since the inner diameter of the bypass chamber 71 is formed to be larger than the outer diameter of the front stopper 30, and the front stopper 30 is in a state of being supported coaxially with the bypass chamber 71 by the plurality of linear ribs 74, without the outer peripheral surface 31 of the front stopper 30 making contact with the inner peripheral surface 73 of the bypass chamber 71.

Thereby, a medicinal solution flow-through space 90 whose dimension in the radial direction is approximately uniform over the circumferential direction is formed between the outer peripheral surface 31 of the front stopper 30 and the inner peripheral surface 73 of the bypass chamber 71. This medicinal solution flow-through space 90 exists over the regions in which the linear ribs 74 are not formed in the circumferential direction of the bypass chamber 71, that is, a total of four medicinal solution flow-through spaces 90 are formed over ranges of approximately 90° in the circumferential direction between adjacent linear ribs 74.

Due to this medicinal solution flow-through space 90 being formed between the outer peripheral surface 31 of the front stopper 30 and the inner peripheral surface 73 of the bypass chamber 71, the air bubbles that have been concentrated at the upper portion of the medicinal solution M within the outer cylinder 10 are very smoothly guided to the medicinal solution flow-through space 90. That is, since the rear end of the medicinal solution flow-through space 90 opens into the outer cylinder 10 over a predetermined range in the circumferential direction, the air bubbles easily flow into a guide channel of the medicinal solution M without being influenced by the surface tension of the medicinal solution M.

The air bubbles that have been guided into the medicinal solution flow-through space 90 in this manner very naturally move toward the upper part of the combination container/syringe 1 along the inner peripheral surface 73 of the bypass chamber 71, that is, it is possible to easily cause the air bubbles to move to the distal end side of the combination container/syringe 1 without performing the operation of pushing the plunger rod 25 further into the outer cylinder 10 in order to expel the air bubbles to the outside.

Then, the air bubbles are expelled to outside of the combination container/syringe 1 via the guide hole 81 that is formed at the bottom portion 72 of the bypass chamber 71 and the injection needle that communicates with the guide hole 81.

Thereafter, when the plunger rod 25 is pushed further in, the distal end of the front stopper 30 abuts the bottom portion 72 of the bypass chamber 71. At this time, the air bubbles that remain behind in the medicinal solution M are expelled to the outside via the medicinal solution flow-through spaces 90, the radial grooves 76, and the guide hole 81.

In the above combination container/syringe 1, the medicinal solution flow-through spaces 90 are formed over the circumferential direction between the inner peripheral surface 73 of the bypass chamber 71 and the outer peripheral surface 31 of the front stopper 30. For that reason, it is possible to expel the air bubbles to the outside via the medicinal solution flow-through spaces 90 without being influenced by the surface tension of the medicinal solution M. Thereby, it is possible to effectively remove air bubbles in the medicinal solution M.

Hereinabove, the combination container/syringe 1 that is an embodiment of the present invention was described in detail, but provided there is no departure from the technical idea of the present invention, it is not limited thereto and some design modifications can be made.

Figure 6:
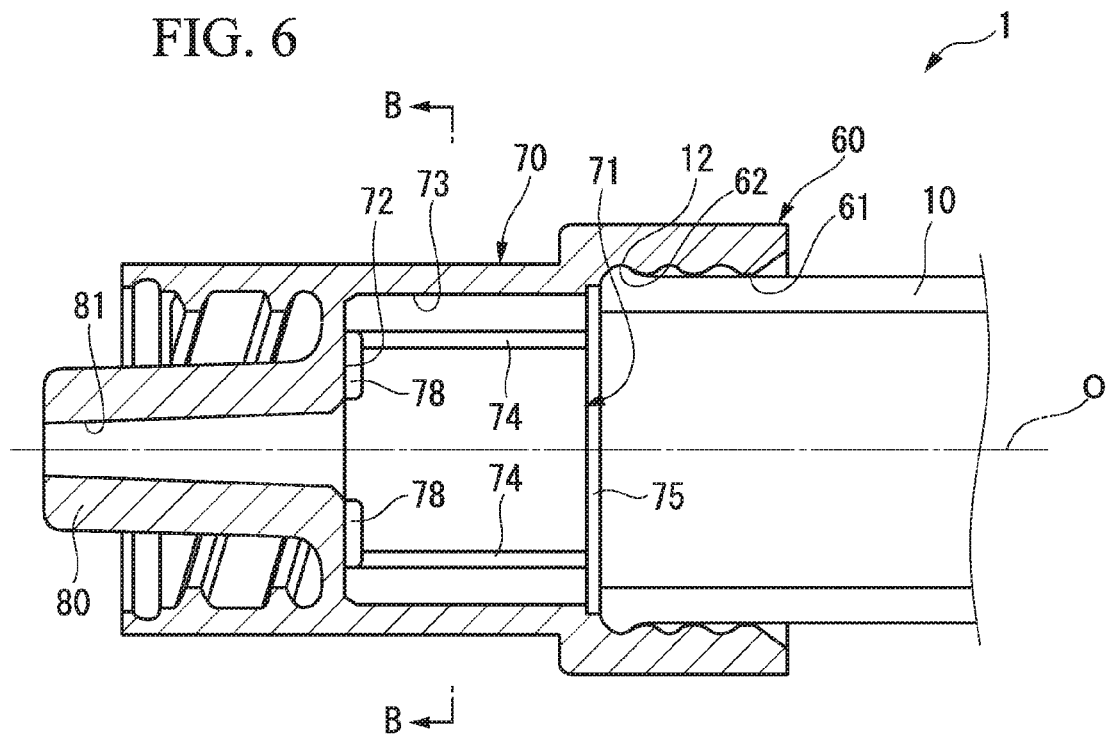
FIG. 6 is an enlargement of the cylindrical tip in the combination container/syringe in the first modification of the present invention.
Figure 7:
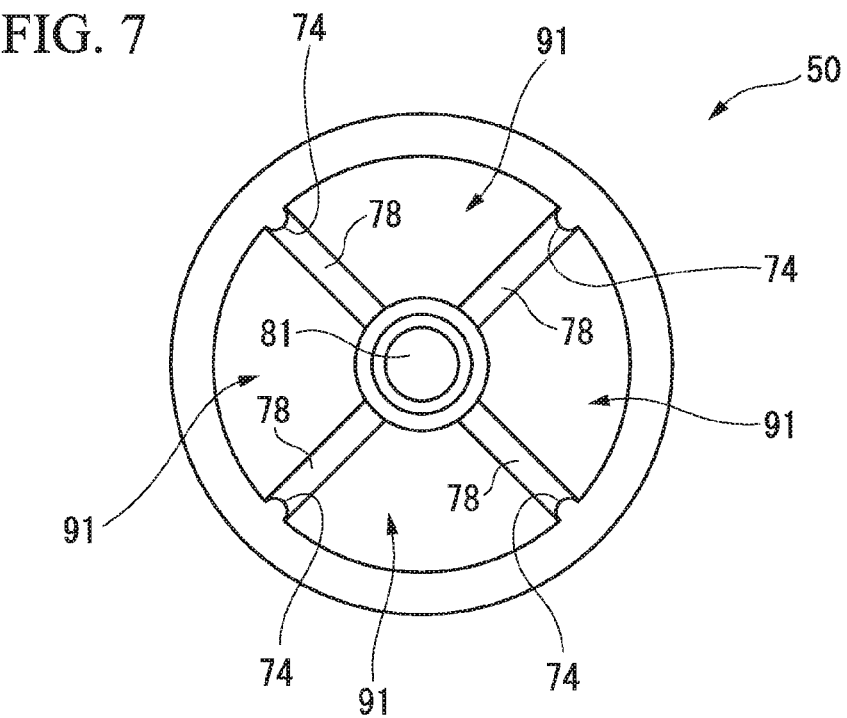
FIG. 7 is a cross-sectional view along B-B in FIG. 6.

For example, in the aforementioned embodiment, the example was described of the radial grooves 76 being formed in the bottom portion 72 of the bypass chamber 71. However, for example, as a first modification, as shown in FIG. 6 and FIG. 7, radial ribs 78 that extend in the radial direction continuously from each of the distal ends of the plurality of linear ribs 74 may be formed at the bottom portion 72 of the bypass chamber 71. These radial ribs 78 are formed in a plurality spaced apart in the circumferential direction similarly to the linear ribs 74, and their end portions on the inner side in the radial direction are connected to the opening of the guide hole 81.

In the state of the front stopper 30 having moved completely within the bypass chamber 71, the distal end of the front stopper 30 abuts the radial ribs 78, and a fan-shaped space 91 with an approximate fan-like shape that is connected to the guide hole 81 is formed between adjacent radial ribs 78 as shown in FIG. 7. Since the flow surface area of a fluid in this fan-shaped space 91 is greater compared to the radial groove 76 of the aforementioned embodiment, it is possible to more smoothly lead bubbles that have remained behind in the medicinal solution M and the medicinal solution M during injection to the guide hole 81.

Figure 8:
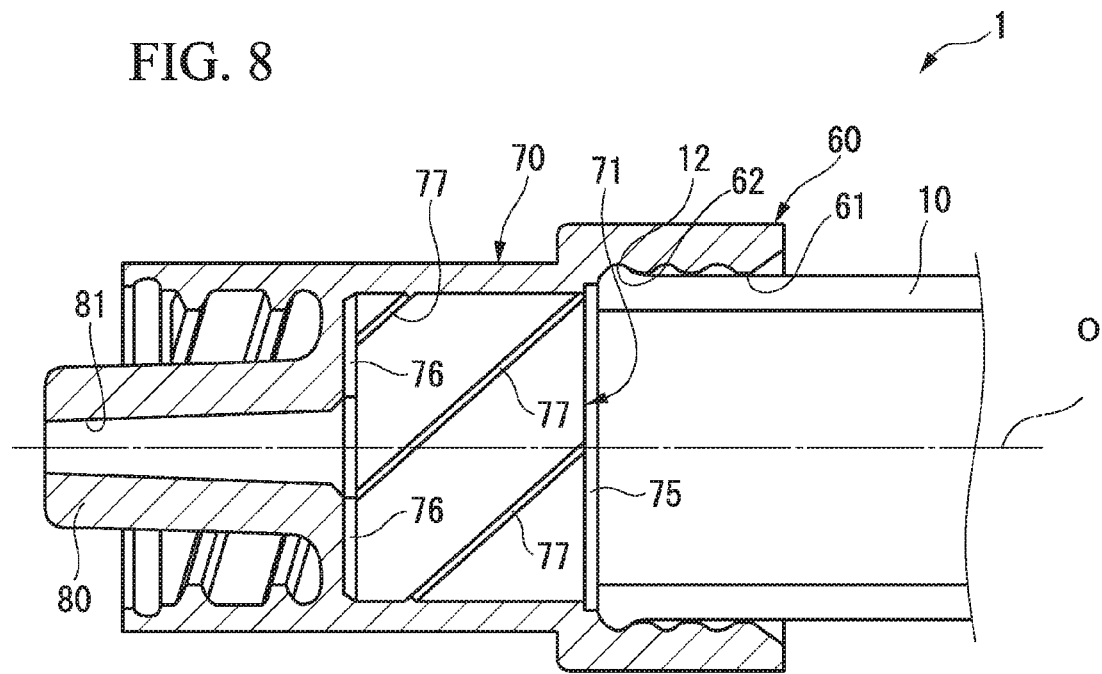
FIG. 8 is an enlargement of the cylindrical tip in the combination container/syringe in the second modification of the present invention.

Moreover, in the aforementioned embodiment, the example was described of the linear ribs 74 being formed on the inner peripheral surface 73 of the bypass chamber 71, but it is not limited thereto, and for example, as shown in FIG. 8 as a second modification, spiral ribs 77 that severally have a spiral shape that twists in the circumferential direction as it heads to one end side in the axial line O direction may be formed on the inner peripheral surface 73 of the bypass chamber 71. In this case as well, when the front stopper 30 is housed in the bypass chamber 71, since it is possible to form the medicinal solution flow-through space 90 between the adjacent spiral ribs 77 similarly to the aforementioned embodiment, it is possible to lead the air bubbles in the medicinal solution M to the outside more smoothly. Also, in the case of these spiral ribs 77, since the air bubbles come to be circulated in the circumferential direction in addition to the axial line O direction, it is possible to improve the velocity of circulation of the air bubbles, and so it is possible to prevent air bubbles adhering to the spiral ribs 77 themselves and remaining behind.

Note that with regard to the shape and dimensions of the front stopper 30, in order to improve slidability within the outer cylinder 10, and in order to facilitate removal of air bubbles, the shape of the distal end at the outer side in the radial direction of the annular convex portion 32 that contacts the inner peripheral surface of the outer cylinder 10 and the inner peripheral surface 73 of the bypass chamber 71 is preferably designed to be as small as possible in a range of being able to maintain the air tightness of the combination container/syringe 1.

Also, the number of the aforementioned annular convex portions 32 is preferably set to be two to five so that the front stopper 30 can maintain the proper orientation within the outer cylinder 10 and within the bypass chamber 71.

Moreover, it is preferable to set the outer diameter of the annular concave portion 33 to be a large as possible within a range that does not contact the inner peripheral surface of the outer cylinder 10 and the inner peripheral surface 73 of the bypass chamber 71. Thereby, it is possible to reduce the amount of the medicinal solution M that remains behind in the annular concave portion 33 when the front stopper 30 has moved to the inside of the bypass channel 71.

EMBODIMENTS

Hereinbelow, the effects of the present invention shall be described with embodiments.

Figure 9:
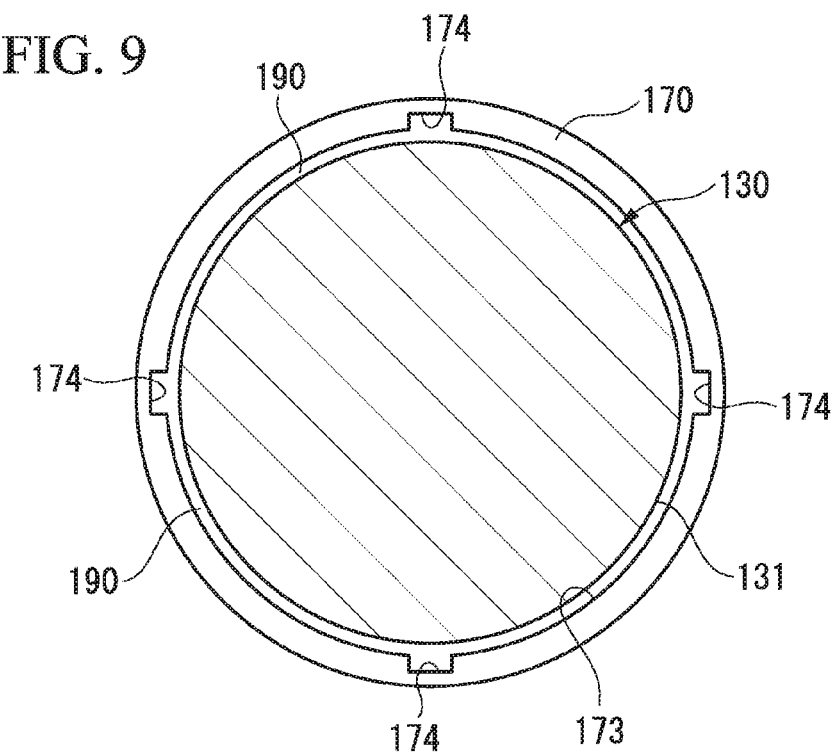
FIG. 9 is a cross-sectional view perpendicular to the axial line in the bypass chamber of a conventional combination container/syringe, and is a drawing that describes the state of the front stopper having moved into the bypass chamber.

FIG. 9 is a cross-sectional view that is perpendicular to the axial line in the bypass chamber of a conventional combination container/syringe, and is a drawing that describes the state of the front stopper having moved into the bypass chamber. That is to say, this drawing shows a conventional combination container/syringe in the same situation as FIG. 5 in the combination container/syringe 1 of the present invention.

In FIG. 9, reference numeral 130 denotes the front stopper, which corresponds to the front stopper 30 in the present invention. Also, reference numeral 170 denotes a cylinder portion of the cylindrical tip, and corresponds to the cylinder portion 70 in the present invention. On the other hand, in the case of the conventional combination container/syringe, a plurality of bypass grooves 174 that indent toward the outer side in the radial direction and extend in a linear shape over the entire region in the axial line direction of the bypass chamber are formed in the inner peripheral surface 173 of the bypass chamber that is formed in the inside of the cylinder portion 70. In the example of FIG. 9, a total of four bypass grooves 174 are formed at an interval of 90° in the circumferential direction. The medicinal solution is guided to the injection needle through a medicinal solution flow-through space 190 that consists of a gap that is formed between the inner peripheral surface 173 of the bypass chamber and the outer peripheral surface 131 of the front stopper 130, and the bypass groove 174.

Here, with the cross-sectional area (cross-sectional area perpendicular to the axial line in the bypass chamber) in FIG. 9 of the medicinal solution flow-through space 190 in the conventional combination container/syringe being S1, and the cross-sectional area (cross-sectional area perpendicular to the axial line in the bypass chamber) in FIG. 5 of the medicinal solution flow-through space 90 in the combination container/syringe 1 of the present invention being S2, in a combination container/syringe with a typical size (syringe outer diameter of three sizes of 8.65 mm, 12.5 mm and 16.0 mm), S1 was 1.9~2.8 $mm^2$, and S2 was 8.5~11.0 $mm^2$. Also, as a result of further tests, the preferable range of the surface area S2 was 8.0~12.0 $mm^2$.

That is to say, according of the present invention the cross-sectional area of the medicinal solution flow-through space expanded (8.0:2.8=) 2.9 times to (12.0:1.9=) 6.3 times compared with the conventional combination container/syringe. Note that when the surface area S2 is less than 8.0 $mm^2$, remaining air bubbles in the bypass chamber come to be observed, and when the surface area S2 is greater than 12.0 $mm^2$, the amount of the medicinal solution remaining in the bypass chamber increases, and the occurrence of practical problems was confirmed. Therefore, in the present embodiment the preferred range of the surface area S2 was set to 8.0~12.0 $mm^2$.

Also, in the case of the aforementioned combination container/syringe of three sizes, in the conventional combination container/syringe, the ratio of the cross-sectional area S1 of the medicinal solution flow-through space 190 to the cross-sectional area in FIG. 9 of the front stopper 130 (cross-sectional area perpendicular to the axial line in the bypass chamber) was 1.6~4.5%, while in the combination container/syringe 1 of the present invention, the ratio of the cross-sectional area S2 of the medicinal solution flow-through space 90 to the cross-sectional area in FIG. 5 of the front stopper 30 (cross-sectional area perpendicular to the axial line in the bypass chamber) was 5.0~26.3%. In this case as well, when the aforementioned ratio is less than 5.0%, air bubbles come to be observed in the bypass chamber, and when the ratio is greater than 26.3%, the amount of the medicinal solution remaining in the bypass chamber increases, and the occurrence of practical problems was confirmed.

INDUSTRIAL APPLICABILITY

According to the combination container/syringe of the present invention, it is possible to effectively eliminate air bubbles in a medicinal solution by expelling air bubbles in the medicinal solution to the outside without being influenced by the surface tension of the medicinal solution that is filled in the interior thereof.

DESCRIPTION OF REFERENCE NUMERALS 1 combination container/syringe, 10 outer cylinder, 20 finger grip, 25 plunger rod, 30 front stopper, 31 outer peripheral surface, 40 end stopper, 50 cylindrical tip, 61 fitting hole, 71 bypass chamber, 73 inner peripheral surface, 74 linear rib, 77 spiral rib, 80 luer tip, 90 medicinal solution flow-through space, M medicinal solution

The invention claimed is:
1. A combination container/syringe comprising:
an outer cylinder that forms a cylindrical shape extending along an axial line;
a front stopper that is inserted into a distal end side of the outer cylinder;
an end stopper that is inserted into a rear end side of the outer cylinder, and that seals a medicinal solution in a space with the front stopper;
a cylindrical tip that is fitted to an outer periphery of the distal end of the outer cylinder via a fitting hole at a base end side, and that is provided with a bypass chamber that houses the front stopper at the distal end side of the fitting hole, and provided with a luer tip for attaching an injection needle;

a finger grip that is fitted on the rear end side of the outer cylinder; and a plunger rod that is inserted in the outer cylinder from the rear end side of the outer cylinder to be coupled to the end stopper, wherein the bypass chamber has a constant circumferential inner diameter along an entire longitudinal length that is formed larger than an outer circumferential diameter of the front stopper when the front stopper is not housed within the bypass chamber, wherein, on an inner peripheral surface having a circular cross section of the bypass chamber, a plurality of ribs that protrude toward an inside in a radial direction and extend over the entire longitudinal length of the bypass chamber in the axial line direction of the bypass chamber to be capable of making close contact with an outer peripheral surface of the front stopper that has moved to the inside of the bypass chamber are provided, wherein the plurality of ribs are spaced apart in a circumferential direction, wherein when the front stopper is supported in the bypass chamber by the plurality of ribs making close contact with the front stopper, a medicinal solution flow-through space extends in the circumferential direction, wherein the medicinal solution flow-through space is formed by the outer peripheral surface of the front stopper, the inner peripheral surface of the bypass chamber, and each of the plurality of ribs such that the medicinal solution flow-through space extends radially from one rib to an adjacent rib of the plurality of ribs and whose length in the radial direction is uniform over the circumferential direction, air bubbles in the medicinal solution being effectively removed by the medicinal solution flow-through space.

2. The combination container/syringe according to claim 1, wherein the distal ends of the plurality of ribs at a cross section perpendicular to the axial line is arc-shaped.

3. The combination container/syringe according to claim 1, wherein the front stopper has a cross-sectional area perpendicular to the axial line of the bypass chamber and the medicinal solution flow-through space has a cross-sectional area perpendicular to the axial line of the bypass chamber, and wherein a ratio of the cross-sectional area of the medicinal solution flow-through space to the cross-sectional area of the front stopper is 5.0 to 26.3%.

* * * * *